United States Patent [19]

Lévêque et al.

[11] 4,365,638
[45] Dec. 28, 1982

[54] APPARATUS FOR ASCERTAINING THE FIRMNESS OF TISSUE

[75] Inventors: Jean-Luc M. Lévêque, Montfermeil; André H. Abrioux, Drancy, both of France

[73] Assignee: L'Oreal, Paris, France

[21] Appl. No.: 228,443

[22] Filed: Jan. 26, 1981

[30] Foreign Application Priority Data

Feb. 1, 1980 [FR] France ............................. 80 02216

[51] Int. Cl.³ ............................................. A61B 10/00
[52] U.S. Cl. .................................... 128/774; 128/297; 73/37.5; 73/838
[58] Field of Search ............... 128/774, 782, 630, 278, 128/297; 73/37.5, 838; 33/172 R, 169 B, 178 D, 174 A

[56] References Cited

U.S. PATENT DOCUMENTS

| | | | |
|---|---|---|---|
| 1,361,848 | 12/1920 | Green | 33/172 R |
| 2,210,435 | 8/1940 | Ruf | 33/172 R |
| 2,591,443 | 4/1952 | Larson et al. | 128/2 |
| 4,073,294 | 2/1978 | Stanley et al. | 128/278 |
| 4,159,640 | 7/1979 | Leveque | 128/774 |

FOREIGN PATENT DOCUMENTS

| | | |
|---|---|---|
| 733686 | 10/1932 | France. |
| 43561 | 4/1934 | France. |
| 1128462 | 9/1968 | United Kingdom. |
| 588973 | 1/1978 | U.S.S.R. ............................. 128/774 |

OTHER PUBLICATIONS

"Experimental Method for Determining the 2-Dimensional Mechanical Properties of Living Human Skin," Cook et al., Medical and Biological Engineering and Computing, Jul. 1977, pp. 382–390.

*Primary Examiner*—Richard J. Apley
*Assistant Examiner*—J. L. Kruter
*Attorney, Agent, or Firm*—N. Jerome Rudy

[57] ABSTRACT

Apparatus for measuring the firmness of tissue, for example of skin in vivo, comprises a compartment open at one end and having a deformable bulb at the other end to allow the compartment near the open end to be subject to internal suction deforming a portion of skin against which the apparatus is applied to dome upwardly into the compartment. A plunger pressed upwardly by the doming skin actuates a pivotable pointer visible from outside the apparatus.

23 Claims, 3 Drawing Figures

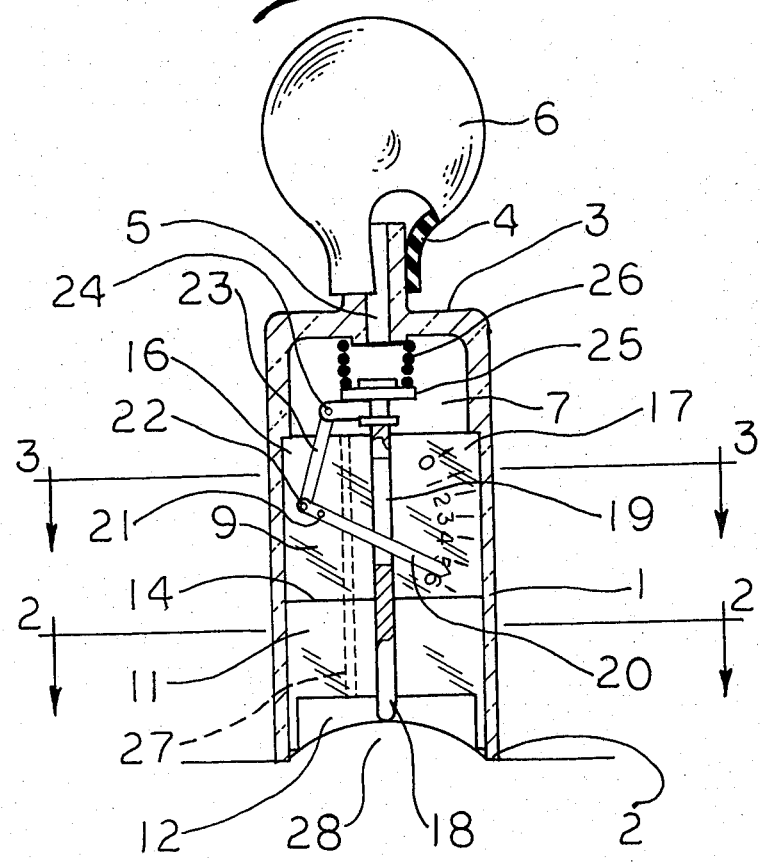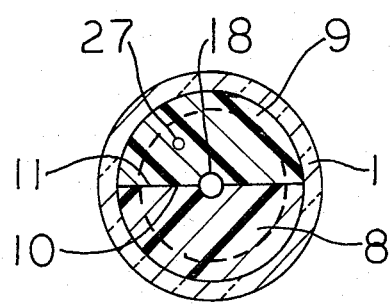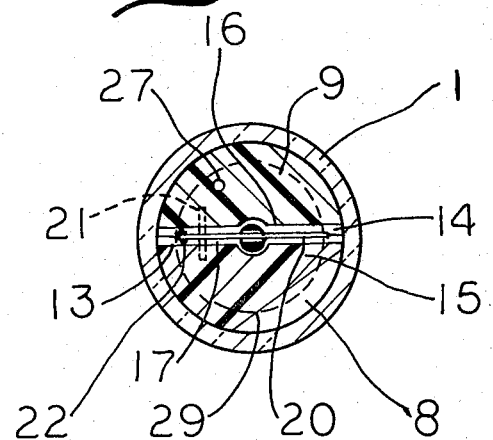

APPARATUS FOR ASCERTAINING THE FIRMNESS OF TISSUE

The present invention relates to an apparatus for ascertaining the firmness of tissues and in particular, living human skin.

It is already known to measure the elasticity of human skin in vitro with a view to obtaining information concerning the structure and qualities of the skin. It has also been already proposed to effect measurements on human skin in vivo by means of a device comprising a bell-shaped glass cup which is applied with its open base on the skin and which has at its end away from the skin, a duct allowing the establishment of low pressure in the cup which tends to raise the skin causing it to assume the shape of a dome or cupola whose dimensions are determined by the displacement of a volume of liquid situated within the cup and in contact with the skin.

Devices of this kind have made it possible to obtain worthwhile information concerning the characteristics of the skin in vivo. However, they have the drawback of being very complex, both in their structure and in their operation, so that they are expensive and can only be used by qualified staff.

It is an object of the present invention to overcome these drawbacks and to provide apparatus for controlling the firmness of tissues and in particular of the skin in vivo, the apparatus being of simple construction and easy application so that it can be operated by anyone.

Accordingly the present invention provides apparatus for ascertaining the firmness of tissue, which apparatus comprises: a compartment capable of being applied against the tissue by its open base: means for establishing suction in the compartment: and means responsive to the dome-shaped deformation of the tissue into the compartment under the effect of said established suction which is adapted to to display an indication in response to said deformation, the said deformation responsive means being comprised of an elongate plunger slidable in the compartment in a direction perpendicularly to the tissue under the effect of the deformation of the tissue: said plunger cooperating with the display means to give an exteriorly visible indication which is dependent on the displacement of the plunger and wherein said means for establishing suction within the compartment includes a deformable bulb.

The plunger is preferably biased towards the open base of the apparatus, i.e. against the tissue, by a weak return spring which is incapable of exerting any noticeably deleterious action on the skin as the skin tends to deform itself under the effect of the suction.

Advantageously, the deformation-responsive means includes indicator means cooperating with the plunger and comprising a pointer displaceable in front of a suitably graduated scale and connected to the plunger by means of a linkage enabling the axial sliding motion of the plunger to be transformed into a rotary motion of the pointer of an increased amplitude.

The compartment is preferably made of a transparent material allowing the indicator means such as the pointer and the scale to be seen.

Preferably, the compartment may have a cylindrical wall at its open base and enclosing two components of a substantially hemi-cylindrical shape, defining between them a central axial passage within which the plunger slides and a radial slot allowing the displacement of the pointer in front of the scale. To avoid the effect of optical distortion due to the presence of a cylindrical lens, a part of the side surface of one of the hemi-cylindrically shaped components may advantageously be made planar to allow convenient reading of the scale and the position of the pointer in relation thereto.

The apparatus of this invention has many applications, particularly in the use of treatments for controlling the suppleness of skin.

The invention will now be described with reference to a particular embodiment, given by way of a non-restrictive example, with reference to the accompanying drawing in which:

FIG. 1 is an axial cross section of the apparatus according to the invention:

FIG. 2 is a transverse cross section along the line II—II of FIG. 1; and

FIG. 3 is a transverse cross section along line III—III of FIG. 1.

The apparatus shown comprises a compartment in the form of a cylindrical component 1 of glass or other transparent plastic material, having an external diameter of the order of 2.5 cm. The base 2 of this component is open towards the bottom whereas the top wall 3 of the component 1 is provided with a central extension collar 4 equipped with an axial duct 5 so as to allow squeezing of a rubber bulb 6, force-fitted on the collar 4, to place the compartment 7 formed by the inner volume of component 1 under low pressure.

Within compartment 7 are two components 8, 9 of a substantially hemi-cylindrical shape made of a transparent plastic material. As may be seen in FIG. 2, these components 8, 9 are joined along a common diametral plane by their adjacent surfaces 10,11. In the lower part of the assembly formed by the two hemi-cylindrical components 8, 9, is a cut-out 12 obtained by two hemi-cylindrical recesses concentrically disposed in the bottom bases of these components 8, 9. Above the adjacent surfaces 10, 11 are cut-outs 13, 14 so that the components 8, 9 are continued by two surfaces 15, 16 extending parallel between themselves at a certain distance to form a radial slot 17. Moreover, provision is made in the components 8, 9 for two longitudinal (i.e. axially extending) semi-circular grooves which come into register to form a central passage along which an elongated plunger 18 is freely slidable in the axial direction. In its part which is displaced within the slot 17 the plunger 18 has a longitudinal slit or port 19 capable of being traversed by a pointer 20 caused to pivot in the diametrical plane. The pivoting is effected around a pivot 21 whose two ends are accommodated in components 8, 9, respectively. In this way, the pointer can move in front of a scale which, as may be seen in FIG. 1, is carried by component 9 and provided with seven scale marks from 0 to 6. The end of pointer 20 is articulated at 22 to a linkage 23 which is itself articulated on a short peripheral arm 24 of the top end of plunger 18. The plunger head beyond arm 24 has a transverse disc 25 biased downwardly by a weak spring 26 supported between the disc 25 and the top wall 3 of component 1.

Finally, a longitudinal passage 27 through component 9 communicates the upper and lower ends of compartment 7 with one another and enables suction established by means of bulb 6 to be applied instantaneously to the lower volume 12.

The functioning is as follows:

The operator grasps the apparatus by means of bulb 6 by squeezing it vigorously and he applies the base 2 of the apparatus against the skin of the person to be tested. He then releases his squeezing pressure and, by the suction cup effect, barrel 1 remains applied against the skin which deforms itself upwardly into the compartment 12 to constitute a dome shaped area 28 whose height is a function of the characteristic of the skin. During this deformation, the dome-shaped skin pushes plunger 18 upwards as viewed in FIG. 1 against the weak spring 26. By virtue of the articulated linkage 23 during this movement, the pointer leaves its initial position on scale 0 to take up its position in front of the scale corresponding the extent (i.e. curvature) of the cup-shaped deformation 28, for instance on scale mark 5 as shown in the drawing.

After the reading has been taken, the apparatus may be withdrawn from the skin by exerting a sufficiently strong upward pulling action.

To facilitate the reading of the scale marks which are preferably printed or embossed on side 16 of component 9, the corresponding part of component 8 may be provided with a chordally extending flat face 29 allowing reading without noticeable optical distortion. Instead of being flat, this face may have any appropriate shape allowing, for instance, a magnifying effect to be obtained.

Although the invention has been described with reference to a particular embodiment, it shall be duly understood that it is in no way limited thereto and that various modifications of shape or material may be brought to bear thereon without thereby departing from its scope as defined by the following claims.

We claim:

1. In apparatus for ascertaining the firmness of tissue which apparatus comprises: (a) a compartment having an open base capable of being applied on the tissue whose firmness is to be ascertained; (b) means associated with said compartment (a) for establishing depressurized suction therein, which means are effective to cause the deformation of tissue against which the said open base of compartment (a) is applied into a dome-shaped configuration of the tissue into said compartment; and (c) means responsive to the dome-shaped deformation of the tissue of said compartment (a) under said suction effect which are adapted to display an indication responsive to said tissue deformation; the improvement wherein
    (i) said tissue deformation-responsive means (c) comprises an elongate plunger in said compartment (a); there being
    (ii) means within said compartment (a) for mounting said plunger (i) therein for longitudinal displacement thereof perpendicularly to the tissue under the effect of its own deformation;
    (iii) display means cooperative with and indicative of the displacement of said plunger (i) relative to extent of tissue deformation into said compartment (a);
    (iv) means operatively connecting said plunger (i) with said display means (iii); and
    (v) means enabling the visualization and seeing of said display means (iii) from the outside of said compartment (a) in order to facilitate the appreciation and reckoning of the position of the display means in its relative responsiveness to the displacement of said plunger (i).

2. The improved apparatus of claim 1, wherein said display means (iii) comprises:

(viii) a pointer actuable by said means (iv) operatively connecting said display means (iii) with said plunger (i); and
    (ix) indicia positioned so that said pointer (viii) is displaced in front of the said indicia.

3. The improved apparatus of claim 2, wherein:
    the said pointer (viii) is pivotable; and
    said means (iv) operatively connecting said plunger (i) with said pointer (viii) is comprised of:
    (x) linkage means which are articulated to and with one end of said pointer (viii) as well as to and with one end of said plunger (i).

4. The improved apparatus of claim 2, wherein said compartment (a) has:
    (xi) transparent walls of cylindrical configuration; and
    (xii) an assembly of two generally hemi-cylindrical components therewithin; with said hemi-cylindrical components (xii) being so formed as to define between them
    (xiii) a central passage that is adapted to slidably receive said plunger (i); and
    (xiv) means defining a diametrically-extending slot to said passage (xiii); there being also included within said hemi-cylindrical components (xii)
    (xv) means pivotably supporting said pointer (viii) for movement in said diametrically-extending slot (xiv).

5. The improved apparatus of claim 4, wherein said generally hemi-cylindrical components (xii) are transparent.

6. The improved apparatus of claim 4, wherein one of said two generally hemi-cylindrical components (xii) has:
    (xvi) a side forming a wall of said diametrally-extending slot (xiv); and said side (xvi) includes
    (xvii) a graduated scale in front of which said pointer (viii) moves during pivoting.

7. The improved apparatus of claim 6, wherein the defined one of the two generally hemi-cylindrical components (xii) has, in front of said graduated scale (xvii):
    (xviii) a flat face allowing the graduated scale (xvii) to be observed from outside the said compartment (a) without significant optical distortion.

8. An improved apparatus in accordance with that of claim 1 and including, in addition thereto and further combination therewith:
    (vii) resilient means spring biasing said plunger (i) towards the open base of said compartment (a) to ensure positive contact of the plunger with the tissue against which said open base is applied.

9. An improved apparatus in accordance with that of claim 1 wherein said means (b) for establishing said suction within the compartment (a) comprise
    (vi) a deformable bulb connected with and capable of evacuating said compartment (a) when it is pressed upon tissue undergoing firmness ascertainment testing.

10. An improved apparatus in accordance with that of claim 9 and including, in addition thereto and further combination therewith:
    (vii) resilient means spring biasing said plunger (i) towards the open base of said compartment (a) to ensure positive contact of the plunger with the tissue against which said open base is applied.

11. The improved apparatus of claim 9, wherein said display means (iii) comprises:

(viii) a pointer actuable by said means (iv) operatively connecting said display means (iii) with said plunger (i); and (ix) indicia positioned so that said pointer (viii) is displaced in front of the said indicia.

12. The improved apparatus of claim 11, wherein the said pointer (viii) is pivotable; and
said means (iv) operatively connecting said plunger (i) with said pointer (viii) is comprised of:

(x) linkage means which are articulated to and with one end of said pointer (viii) as well as to and with one end of said plunger (i).

13. The improved apparatus of claim 11, wherein said compartment (a) has:

(xi) transparent walls of cylindrical configuration; and (xii) an assembly of two generally hemi-cylindrical components therewithin; with said hemi-cylindrical components (xii) being so formed as to define between them (xiii) a central passage that is adapted to slidably receive said plunger (i); and (xiv) means defining a diametrally-extending slot to said passage (xiii); there being also included within said hemi-cylindrical components (xii)

(xv) means pivotably supporting said pointer (viii) for movement in said diametrically-extending slot (xiv).

14. The improved apparatus of claim 13, wherein one of said two generally hemi-cylindrical components (xii) has:

(xvi) a side forming a wall of said diametrally-extending slot (xiv); and said side (xvi) includes (xvii) a graduated scale in front of which said pointer (viii) moves during pivoting.

15. The improved apparatus of claim 14, wherein the defined one of the two generally hemi-cylindrical components (xii) has in front of said graduated scale (xvii):

(xviii) a flat face allowing the graduated scale (xvii) to be observed from outside the said compartment (a) without significant optical distortion.

16. The improved apparatus of claim 13, wherein said generally hemi-cylindrical components (xii) are transparent.

17. An improved apparatus according to any one of those of claims 2–15, inclusive, wherein said plunger (i) includes:

(xix) means defining an oblong central port slit portion which is traversed by said pointer (viii).

18. An improved apparatus according to any one of those of claims 1–15, inclusive wherein
said compartment (a) has:
(xxi) first and second ends, with
said open base in said compartment (a) being at the said second end thereof.

19. An improved apparatus according to any one of those of claims 4–15, inclusive, wherein at least one of said generally hemi-cylindrical components (xii) includes:

(xx) means defining a longitudinal passage therein which is disposed to run generally in the lengthwise end-to-end direction of said compartment (a); with
said passage defining means (xx) communicating between the ends of the said compartment (a) which are disposed to and at either end of said assembly formed by the two generally hemi-cylindrical components (xii).

20. An improved apparatus according to any one of those of claims 9, 10, 11, 12, 13, 14, 16 or 15 wherein said compartment (a) has:
(xxi) first and second ends, with
said deformable bulb (vi) being at the said first end of said compartment (a) and said open base in the compartment being at the said second end thereof.

21. In apparatus for ascertaining the firmness of tissue which apparatus comprises: (a) a compartment having an open base capable of being applied on the tissue whose firmness is to be ascertained; (b) means associated with said compartment (a) for establishing depressurized suction therein, which means are effective to cause the deformation of tissue against which said open base of compartment (a) is applied into a dome-shaped configuration of the tissue into said compartment; and (c) means responsive to the dome-shaped deformation of the tissue in said compartment (a) under said suction effect which are adapted to display an indication responsive to said tissue deformation; the improvement wherein (i) said tissue deformation-responsive means (c) comprises an elongate plunger in said compartment (a); there being (ii) means within said compartment (a) for mounting said plunger (i) therein for longitudinal displacement thereof perpendicularly to the tissue under the effect of its own deformation;

(iii) display means cooperative with and indicative of the displacement of said plunger (i) relative to extent of tissue deformation into said compartment (a);

(iv) means operatively connecting said plunger (i) with said display means (iii);

(v) means enabling the visualization and seeing of said display means (iii) from the outside of said compartment (a) in order to facilitate the appreciation and reckoning of the position of the display means in its relative responsiveness to the displacement of said plunger (i);

(vii) resilient means spring biasing said plunger (i) towards the open base of said compartment (a) to ensure positive contact of the plunger with the tissue against which said open base is applied;

(viii) a pointer actuable by said means (iv) operatively connecting said display means (iii) with said plunger (i);

(ix) indicia positioned so that said pointer (viii) is displaced in front of said indicia; wherein
the said pointer (viii) is pivotable; and
said means (iv) operatively connecting said plunger (i) with said pointer (viii) is comprised of:

(x) linkage means which are articulated to and with one end of said pointer (viii) as well as to and with one end of said plunger (i).

22. In apparatus for ascertaining the firmness of tissue which apparatus comprises: (a) a compartment having an open base capable of being applied on the tissue whose firmness is to be ascertained; (b) means associated with said compartment (a) for establishing depressurized suction therein, which means are effective to cause the deformation of tissue against which said open base of compartment (a) is applied into a dome-shaped configuration of the tissue into said compartment; and (c) means responsive to the dome-shaped deformation of the tissue in said compartment (a) under said suction effect which are adapted to display an indication responsive to said tissue deformation; the improvement wherein
- (i) said tissue deformation-responsive means (c) comprises an elongate plunger in said compartment (a); there being
- (ii) means within said compartment (a) for mounting said plunger (i) therein for longitudinal displacement thereof perpendicularly to the tissue under the effect of its own deformation;
- (iii) display means cooperative with and indicative of the displacement of said plunger (i) relative to extent of tissue deformation into said compartment (a);
- (iv) means operatively connecting said plunger (i) with said display means (iii);
- (v) means enabling the visualization and seeing of said display means (iii) from the outside of said compartment (a) in order to facilitate the appreciation and reckoning of the position of the display means in its relative responsiveness to the displacement of said plunger (i);
- (vii) resilient means spring biasing said plunger (i) towards the open base of said compartment (a) to insure positive contact of the plunger with the tissue against which said open base is applied;
- (viii) a pointer actuable by said means (iv) operatively connecting said display means (iii) with said plunger (i);
- (ix) indicia positioned so that said pointer (viii) is displaced in front of the said indicia; wherein the said pointer (viii) is pivotable; and
said means (iv) operatively connecting said plunger (i) with said pointer (viii) is comprised of;
- (x) linkage means which are articulated to and with one end of said pointer (viii) as well as to and with one end of said plunger (i);

with the said compartment (a) having:
- (xi) transparent walls of cylindrical configuration; and
- (xii) an assembly of two generally hemi-cylindrical components therewithin; with said hemi-cylindrical components (xii) being so formed, as to define between them

- (xiii) a central passage that is adapted to slidably receive said plunger (i); and
- (xiv) means defining a diametrally-extending slot to said passage (xiii); there being also included within said hemi-cylindrical components (xii)
- (xv) means pivotally supporting said pointer (viii) for movement in said diametrically-extending slot (xiv); with one of said two generally hemi-cylindrical components (xii) having:
- (xvi) a side forming a wall of said diametrally-extending slot (xiv); with said side (xvi) including
- (xvii) a graduated scale in front of which said pointer (viii) moves during pivoting; and
- (xviii) in front of said graduated scale (xvii), a flat face allowing the said graduated scale to be observed from outside the said compartment (a) without significant optical distortion;

the said hemi-cylindrical components (xii) also being transparent; and also wherein
the said plunger (i) includes:
- (xix) means defining an oblong central port slit portion which is traversed by said pointer (viii); with the said defined one of the two generally hemi-cylindrical components (xii) also includes:
- (xx) means defining a longitudinal passage therein which is disposed to run generally in the lengthwise end-to-end direction of said compartment (a); with said passage defining means (xx) communicating between the ends of the said compartment (a) which are disposed to and at either end of said assembly formed by the two generally hemi-cylindrical components (xii).

23. An improved apparatus in accordance with either of those of claim 21 or claim 22, wherein said means (b) for establishing said suction within the compartment (a) comprise:
- (vi) a deformable bulb connected with and capable of evacuating said compartment (a) when it is pressed upon tissue undergoing firmness ascertainment testing.

* * * * *